United States Patent [19]

Nicholson et al.

[11] Patent Number: 4,616,656
[45] Date of Patent: Oct. 14, 1986

[54] SELF-ACTUATING BREAST LESION PROBE AND METHOD OF USING

[76] Inventors: James E. Nicholson, 14 Meadowdam Rd., Lincoln, Mass. 01773; Roland F. Gatturna, 169 Kendall St., Walpole, Mass. 02081

[21] Appl. No.: 713,613

[22] Filed: Mar. 19, 1985

[51] Int. Cl.⁴ ............................................. A61B 5/00
[52] U.S. Cl. ................................... 128/630; 128/653
[58] Field of Search ............... 128/418, 784–785, 128/774, 630.1, 653, 303.16, 303.17; 604/164–169

[56] References Cited

U.S. PATENT DOCUMENTS

| | | | |
|---|---|---|---|
| 2,022,065 | 11/1935 | Wappler | 128/303.17 |
| 2,047,535 | 7/1936 | Wappler | 128/303.17 |
| 3,516,412 | 6/1970 | Ackerman | 128/786 |
| 3,890,977 | 6/1975 | Wilson | 128/785 X |
| 4,103,690 | 8/1978 | Harris | 128/786 X |
| 4,327,722 | 5/1982 | Groshong et al. | 604/169 X |
| 4,349,033 | 9/1982 | Eden | 128/774 |
| 4,401,124 | 8/1983 | Guess et al. | 128/660 |
| 4,405,314 | 9/1983 | Cope | 604/164 X |

OTHER PUBLICATIONS

Porstmann, W. et al., "P Wave Synchronous Pacing Using Anchored Atrial Electrode Implanted without Thoracotomy", Amer. Jour. Cardiology, vol. 30, pp. 74–76, Jul. 11, 1972.
44

*Primary Examiner*—Kyle L. Howell
*Assistant Examiner*—Francis J. Jaworski
*Attorney, Agent, or Firm*—Morris Kaplan

[57] ABSTRACT

A probe sheath and probe wire having a memory hook and soft flexibility are used to locate a small presymptomatic breast lesion, wherein the wire is sheathed within the sheathing cannula and both are inserted into the body tissue and directed to the site of the lesion. Thereafter the wire is extended through the sheath to assume its memory configuration and its location is determined mammographically. If re-positioning is necessary the wire may be retracted into the sheath and then extended and re-anchored after the wire and sheath are directed to a new position. When the probe wire location is acceptable the cannula is removed and the probe wire is left as a marker for surgical excision of the lesion.

20 Claims, 4 Drawing Figures

SELF-ACTUATING BREAST LESION PROBE AND METHOD OF USING

TECHNICAL FIELD

The present invention relates to lesion location within the body and is especially adapted to detection and location of presymptomatic, non-palpable lesion within the female breast.

BACKGROUND OF THE INVENTION

It is known to relay on mammography in conjunction with a needle cannula having a probe wire therein for localization of a presymptomatic, non-palpable breast lesion. In such procedure, a needle cannula having a wire sheathed therein is inserted so that the distal end of the needle is located at about the tissue area of pathological alteration; desirably at less than 2 cm from the lesion. A mammogram is then taken to confirm the probe position. If the probe does not accurately relate to the lesion, then the probe is relocated, or an additional probe may be inserted, and a further mammogram is taken. When the probe location is acceptable, then the cannula needle is removed and the patient transferred to surgery for lesion excision.

Obviously, removal of the lesion with minimal tissue damage will relate to maintenance of the wire's distal end as determined by the final mammographic examination.

In the instance of a straight wire probe, as for instance the Bueno Probe manufactured by Micro-Machining of Claremont, N.H., taping-down or otherwise fixing an extending portion of the wire does not prevent movement of the wire's distal end upon breast movement and expansion after the initial probe procedure.

It is known to use a probe wire having a bend at its distal end whereby when the cannula needle is removed, the bend or hook portion anchors in the tissue. Such known bent or hooked probe wires are for instance the Frank Breast Biopsy Probe manufactured by Randall-Faichney of Avon, Mass., and the Kopans Probe manufactured by Cook, Inc. of Bloomington, Ind. These known, hooked type localization probes have a disadvantage in that once the wire is anchored it can only be removed by resection. Thus, the Kopans Probe would have to be mammographically finally positioned whole its wire element is completely sheathed in the cannula needle. If, after cannula removal, the resultant hook location is unsatisfactory, then another probe means must be inserted.

Hence, the known bent or hooked probe wires have in effect a one-time anchoring use. Further, if more than one wire is relied on, then each anchored wire must be surgically removed with consequent excision of tissue in addition to that of the lesion.

SUMMARY OF THE INVENTION

The present invention is especially directed to improved means and method for confirming location of a presymptomatic, non-palpable breast lesion by placement and manipulation of a probe comprised of a cannula needle and probe wire therewith.

It is an object of the present invention that the probe wire be of novel construction.

It is a further object of the invention that the novel probe wire comprise inherent anchoring means that inhibit accidental dislodgement of the wire upon ordinary and conventional movement of the body containing the lesion.

It is another object of the invention tha the anchoring means comprise a yieldable memory device that is manually retractable from an anchored location to a sheathed location within the cannula; as for relocation with respect to the lesion.

It is a further object of the invention that the novel probe wire bear graduated scale markings at its distal and proximal end portions.

It is yet another object of the invention that a positive lock means be provided at the proximal end of the probe wire.

It is an object of the invention that the novel and improved cannula needle and wire probe therewith be an uncomplicated combination of simple structural elements, inexpensive and easy to manufacture and simple to manipulate in lesion localization.

For a more fully developed presentation of the invention, and a preferred embodiment thereof, reference is made to the following descriptive matter and attached drawings.

DETAILED DESCRIPTION OF THE INVENTION

Figure 1:
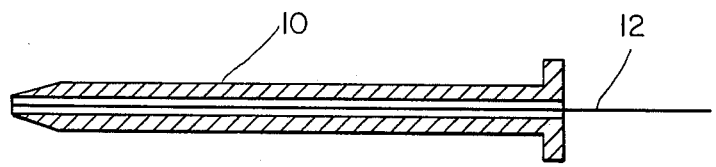
FIG. 1 is a view of the probe wire of the invention assembled with a longitudinal section of the cannula and, for clarity of display, in an exaggerated dimensional relationship.

Referring to the drawings which show a preferred embodiment of the invention and wherein like numerals indicate like elements of structure, there is shown in FIG. 1 a conventional probe cannula 10 and an improved probe wire 12 in assembled relationship preparatory to insertion of the unit into the body tissue for lesion location. For purposes of clarity, the dimensional relationship of the cannula and probe wire are exaggerated. In actuality, the wire has a close but easily slidable fit; the wire being for instance approximately 0.015 inches in diameter and the cannula being of 20 gauge. Preferably, the wire is coated, as with a silicone or teflon, for purposes of lubricity and electrical insulation.

As shown in FIG. 1, the probe wire lies straight in its cannula sheathing and as so assembled, the unit is inserted into the body tissue to a location whereat the distal end lies hopefully at about 2 cm from the lesion as previously determined by mammography. The latter is repeated to confirm the accuracy of the probe location. If the desired accuracy is not confirmed, then the probe unit is repositioned and the steps repeated until the desired confirmation is attained.

Figure 2:
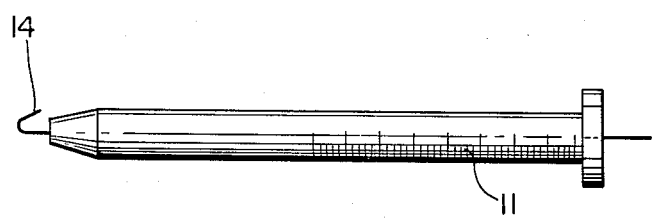
FIG. 2 is a view of the self-actuating hook or memory portion of the probe wire pushed through the cannula as at an anchored location.

Following such confirmation, the wire probe end is pushed forward of its sheathed position as illustrated in FIG. 2. Note that the freed wire end 14 has assumed the shape of a relatively small curl or hook whereby the probe wire anchors itself in the tissue at the lesion site.

The probe wire is preferably manufactured of a material having the memory characteristic of such relatively small curl or hook at its freed distal end.

Materials broadly possessing such a memory characteristic and suitable for the inventive purpose are known; as for instance Nitinol, a NiTi alloy produced by Raychem Corp. of Menlo Park, Calif. Such titanium or titanium alloy materials have additional characteristics of being sufficientlyr rigidly whereby to inhibit dislodgement upon subsequent normal and ordinary movement and handling of the body portion in which the lesion is located; are difficult to cut; and will not easily break whereas accidental rupture of the probe wire, as is known to occur with prior art wires, would severely complicate the procedure of lesion excision with minimal damage to the containing tissue. The probe wire could also be formed of a bimetal material that is normally straight but is responsive to body heat for actuation to the hook formation.

In continuation of the localization procedure, a mammographic determination is made to confirm accuracy of the anchored distal end of the probe wire to less than 2 cm from the lesion site.

Assuming that such accuracy is not confirmed, a relocation of the probe wire is desirable in order to effect an optimum surgical result. Obviously, with prior art one-time anchoring usage, such relocation is impossible; either the surgeon proceeds with the less than optimally desirable locater guide or a new round of probe unit insertion/mammographic confirmation is initiated.

However, in the instant case such relocation is possible. The aforedescribed probe wire which is strong enough to prevent accidental dislodgement and breaking, and is tough to cut also has an additional and critical characteristic of being flexibly soft and responsive to manual urging whereby the anchored distal end will release and easily slide from its grasp of tissue and retract into its fully sheathed location within the cannula without further tissue damage.

It is precisely such latter characteristic that most significantly distinguishes the instant probe wire from the prior art. In this connection, it is of interest that the U.S. Pat. Nos. 4,307,723 to Finney and 3,539,034 to Tafeen each disclose a catheter whose distal end possesses a memory characteristic, that U.S. Pat. No. 3,943,932 to Woo discloses an acupuncture needle that may possess a memory characteristic and that U.S. Pat. No. 4,230,123 to Hawkins discloses what is described as a J-wire which is inserted through a cannula for fixing the distal end of said cannula.

Having finally located the probe wire with confirmed accuracy, the cannula is removed. As is known in the art, one may then tape down the proximal portion of the probe wire that extends from the body to thereby further inhibit wire displacement upon subsequent body handling and transportation. However, it is preferred that a more positive means be relied on to both further inhibit wire displacement and to prevent tissue from rising over a section of such extending proximal wire that due to prior manipulation may have become non-sterile.

Figure 4:
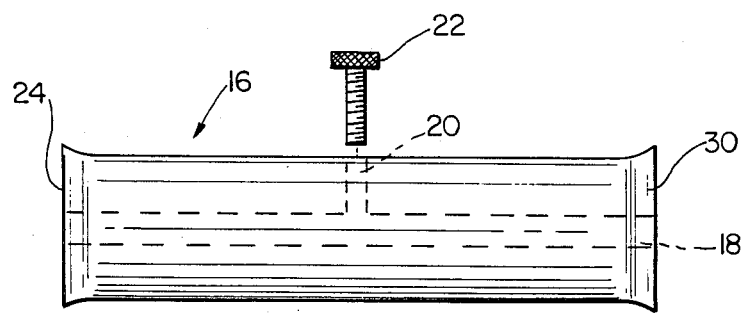
FIG. 4 is an exploded view of a probe wire clamp member.

Such a more positive means may comprise a biased clip type member but a preferred clamp means is illustrated in FIG. 4 wherein member 16 has an aperture 18 axially therethrough and a threaded aperture 20 extending normal to aperture 18 and intersecting same. A threaded clamp-screw 22 operatively associates with aperture 20. The cross-sectional configuration of said clamp means is broadly not material except that, to facilitate handling, the peripheral surface may be ribbed or knurled or, as shown, may be provided with flange portions 30. In use, the clamp means is positioned with the proximal portion of the finally anchored probe wire extending through the axially disposed aperture, the end face 24 of the clamp is brought to bear on the body surface, whereby to prevent body tissue from rising over any of such proximal portion extending from the body, and the screw tightened to thereby fix the parts.

Graduations 26 are provided on the proximal extent of the probe wire. These markings indicate both the depth of the probe wire's distal end when anchored and the depth of the probe unit's distal end when the wire is properly sheathed in the cannula.

Figure 3:
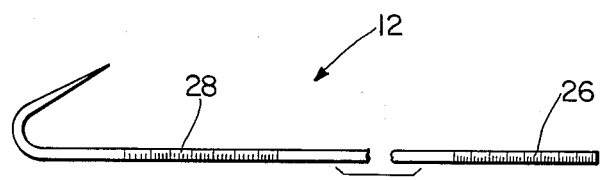
FIG. 3 is a view of a preferred embodiment of the probe wire showing graduated scale markings thereon.

Graduations 28 on the extended distal portion of the probe wire are an indication to the surgeon as to relation of incision to the distal end of the wire. Such graduations 28 may extend further along the distal end than is illustrated in FIG. 3.

Graduations 11 on the cannula are provided whereby to indicate the depth of cannula penetration into the body.

Such graduations may be etchings and may be color coded.

The embodiments shown and described are only illustrative of the present invention and are not to be construed as being delimitive thereof; since once apprised of the invention, changes in structure would be readily apparent to one skilled in the art. Hence, the present invention includes all modifications of structure encompassed within the spirit and scope of the following claims.

We claim:

1. A method of locating a lesion, especially a method for locating a presymptomatic, non-palpable breast lesion, comprising the steps of:
    (A) mammographically determining the probable location of such lesion;
    (B) selecting a probe wire that has at its distal end a relatively small memory hook and a predetermined degree of soft flexibility;
    (C) sheathing the probe wire in a needle cannula whereat the wire assumes the straight configuration of the cannula and the distal ends of the wire and cannula are in a predetermined relationship as evidenced by observation of graduated scale markings on the proximal portion of the wire;
    (D) maintaining such determined relationship and initially inserting the assembled cannula and probe wire unit into the body tissue to a depth whereat said distal endsd are at about the site of said lesion;
    (E) mammographically determining if placement of such distal ends is within a predetermined spacing with regard to the lesion;
    (F) repositioning the unit and mammographically determining each aforedescribed placement of said unit until the desired accuracy is achieved;
    (G) solely moving the probe wire forwardly to an extent, as determined by further observation of said graduated scale markings, whereby to only free the distal end portion having the memorty hook and whereby the distal end of the probe wire assumes the hook configuration to thereby anchor itself in the tissue;
    (H) mammographically determining the spatial relationship of the anchored end of the probe wire to the lesion with regard to a desired accuracy thereof;

(I) relying on said characteristic of soft flexibility of the probe wire, manually actuating the probe wire to release and easily slide from its anchored position in the tissue to a fully sheathed location within the cannula at said predetermined relationship of the distal ends without injury to the tissue when said desired accuracy has not been effected; and (J) repositioning the unit as aforedescribed, reanchoring the probe wire as aforedescribed, and repeating the aforedescribed mammographic determinations until the desired accuracy of the spatial relationship of the anchored end of the probe wire to the lesion site is effected.

2. The method of claim 1 comprising the additional steps of:

(K) completely withdrawig and removing the cannula needle; and (L) fixing the probe wire by clamping a lock means onto the wire and simultaneously in a position whereat one surface of the lock means bears on the body containing the lesion;

whereby, during subsequent transportation and handling of the body, to further inhibit dislodgement of the probe wire and to prevent the body tissue from covering the proximal portion of the probe wire that may have become non-sterile.

3. The method of claim 1 wherein the depth of unit insertion, as described in (D), guided by observation of graduated scale markings on the cannula needle.

4. A method of lesion excision comprising:
locating the lesion by the method of claim 1; and
during surgical removal of the lesion, being guided by observation of graduated scale markings on the distal portion of the anchored probe wire.

5. A probe unit adapted for location of a lesion, and especially for location of a presymptomatic, non-palpable breast lesion, comprising:

(A) a tubular needle cannula adapted for insertion into a body to the site of said lesion;

(B) a probe wire in the form of a simple straight wire closely fitted within, and freely slidable through, said cannula;

(C) said probe wire possessing a memory hook shape at its distal end whereby such end assumes the straight configuration of the cannula when sheathed therein and being dimensioned so as to pierce the body tissue while simultaneously assuming its normal hook configuration when pushed through the cannula to thereby anchor itself in the tissue at the lesion when the probe unit of cannula and probe wire therein has previously been inserted into the body at about the lesion site;

(D) said probe wire possessing the further characteristic of a predetermined degree of soft flexibility whereby said wire is adapted to be manually actuated to release and easily slide from a said anchored location to a fully sheathed disposition within the cannula and without undue destruction of surrounding tissue;

(E) whereby the probe unit may be relocated within the body and the probe wire reanchored within the tissue until a desired accuracy is attained with respect to lesion location; and (F) the cannula needle being completely withdrawable from the body and operative association with the probe wire.

6. A probe unit as in claim 5 having in combintion therewith a fixing clamp comprised of:

(G) a member having a first aperture axially therethrough and adapted to accommodate the proximal portion of an anchored probe wire when a cannula needle is withdrawn from the body and removed from operative association with the wire;

(H) a threaded aperture disposed generally normal to and intersecting the first aperture;

(I) a clamping screw operatively associated with the threaded aperture; and (J) a distal face of the member adapted to bear against the body surface through which the anchored probe wire would extend, whereupon the clamp screw would be adapted to lock the proximal portion of said wire and the body surface would be prevented from rising over said extending proximal probe wire portion that may have become non-sterile.

7. A probe unit as in claim 6 wherein the cannula needle has graduated scale markings thereon whereby to determine depth of cannula or probe unit insertion into the body.

8. A probe unit as in claim 6 wherein the probe wire has graduated scale markings on the proximal portion thereof whereby to determine alignment of the distal ends of the assembled cannula and probe wire and whereby to determine the extent to which the probe wire need be pushed through the cannula to only free the memory hook portion for its anchoring function.

9. A probe unit as in claim 6 wherein the probe wire has graduated scale markings on the distal portion thereof whereby during excision of a lesion the surgeon is guided.

10. A probe unit as in claim 5 wherein the cannula needle has graduated scale markings thereon whereby to determine depth of cannula or probe unit insertion into the body.

11. A probe unit as in claim 10 wherein the probe wire has graduated scale markings on the proximal portion thereof whereby to determine alignment of the distal ends of the assembled cannula and probe wire and whereby to determine the extent to which the probe wire need be pushed through the cannula to only free the memory hook portion for its anchoring function.

12. A probe unit as in claim 10 wherein the probe wire has graduated scale markings on the distal portion thereof whereby during excision of a lesion the surgeon is guided.

13. A probe unit as in claim 10 wherein the probe wire is coated with an inert material having predetermined lubricity and electrically insulative values.

14. A probe unit as in claim 5 wherein the probe wire has graduated scale markings on the proximal portion thereof whereby to determine alignment of the distal ends of the assembled cannula and probe wire and whereby to determine the extent to which the probe wire need be pushed through the cannula to only free the memory hook portion for its anchoring function.

15. A probe unit as in claim 14 wherein the probe wire has graduated scale markings on the distal portion thereof whereby during excision of a lesion the surgeon is guided.

16. A probe unit as in claim 14 wherein the probe wire is coated with an inert material having predetermined lubricity and electrically insulative values.

17. A probe unit as in claim 5 wherein the probe wire has graduated scale markings on the distal portion thereof whereby during excision of a lesion the surgeon is guided.

18. A probe unit as in claim 17 wherein the probe wire is coated with an inert material having predetermined lubricity and electrically insulative values.

19. A probe unit as in claim 5 wherein the probe wire is coated with an inert material having predetermined lubricity and electrically insulative values.

20. A probe wire adapted for use with a cannula needle for location of a lesion, and especially for location of a presymptomatic, non-palpable breast lesion, comprising:

a wire of the type possessing a relatively small memory hook at its distal end thereby being adapted to anchor in tissue at a lesion site when such end is pushed from a sheathing cannula needle that has been inserted into a body containing such lesion;

said wire being adapted to assume a straight configuration within a said cannula and being dimensioned so as to pierce the body tissue while simultaneously assuming its memory hook configuration to effect said anchor;

said wire havig a relatively soft flexibility characteristic whereby said distal end when anchored is adapted to be manually actuated to release and slide from such an anchored position to a sheathed location in said cannula without undue damage to the tissue;

said wire having graduated scale markings at its proximal portion whereby to facilitate location of the wire's distal end with respect to the distal end of a cannula needle to be used therewith and whereby to determine the extent to which the wire need be pushed through a said cannula needle in order to free only the memorty hook portion for its anchoring function; and said wire having graduated scale markings at its distal portion whereby with the wire properly located and anchored, the markings are adapted to guide a surgeon during excision of a said lesion.

* * * * *